(12) United States Patent
Kojima et al.

(10) Patent No.: US 12,287,339 B2
(45) Date of Patent: Apr. 29, 2025

(54) ANALYSIS METHOD, MICROORGANISM IDENTIFICATION METHOD, AND TESTING METHOD

(71) Applicant: SHIMADZU CORPORATION, Kyoto (JP)

(72) Inventors: Koichi Kojima, Kyoto (JP); Koichi Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 882 days.

(21) Appl. No.: 17/600,483

(22) PCT Filed: Feb. 19, 2020

(86) PCT No.: PCT/JP2020/006501
§ 371 (c)(1),
(2) Date: Sep. 30, 2021

(87) PCT Pub. No.: WO2020/202861
PCT Pub. Date: Oct. 8, 2020

(65) Prior Publication Data
US 2022/0178941 A1 Jun. 9, 2022

(30) Foreign Application Priority Data
Apr. 3, 2019 (JP) .................. 2019-071663

(51) Int. Cl.
*G01N 33/68* (2006.01)
(52) U.S. Cl.
CPC ..... *G01N 33/6848* (2013.01); *G01N 2560/00* (2013.01)

(58) Field of Classification Search
None
See application file for complete search history.

(56) References Cited

U.S. PATENT DOCUMENTS 8,293,496 B2   10/2012   Govorun et al.

OTHER PUBLICATIONS

International Search Report for PCT/JP2020/006501 dated May 26, 2020 (PCT/ISA/210).
Written Opinion for PCT/JP2020/006501 dated May 26, 2020 (PCT/ISA/237).
First Office Action dated Aug. 2, 2022 from the Japanese Patent Office in JP Application No. 2021-511206.
Office Action dated Nov. 29, 2022 issued by the Japanese Patent Office in Japanese Application No. 2021-511206.

*Primary Examiner* — Xiaoyun R Xu
(74) *Attorney, Agent, or Firm* — Sughrue Mion, PLLC

(57) ABSTRACT

An analysis method incudes: preparing a sample containing microorganisms; placing the microorganisms under a first condition and then performing a first mass spectrometry on a substance produced by the microorganisms; and obtaining information on characteristics or classifications of the microorganisms contained in the sample on a basis of a difference between a first data obtained in the first mass spectrometry and a second data obtained when a second mass spectrometry is performed on a substance produced by the microorganisms after having been placed under a second condition as well as a reference data in which classifications or characteristics of the microorganisms are associated with the data obtained in the mass spectrometry of the microorganisms, in which the first condition and the second condition differ in a sugar concentration or an oxygen concentration in an environment in which the microorganisms are placed.

16 Claims, 11 Drawing Sheets

Specification includes a Sequence Listing.

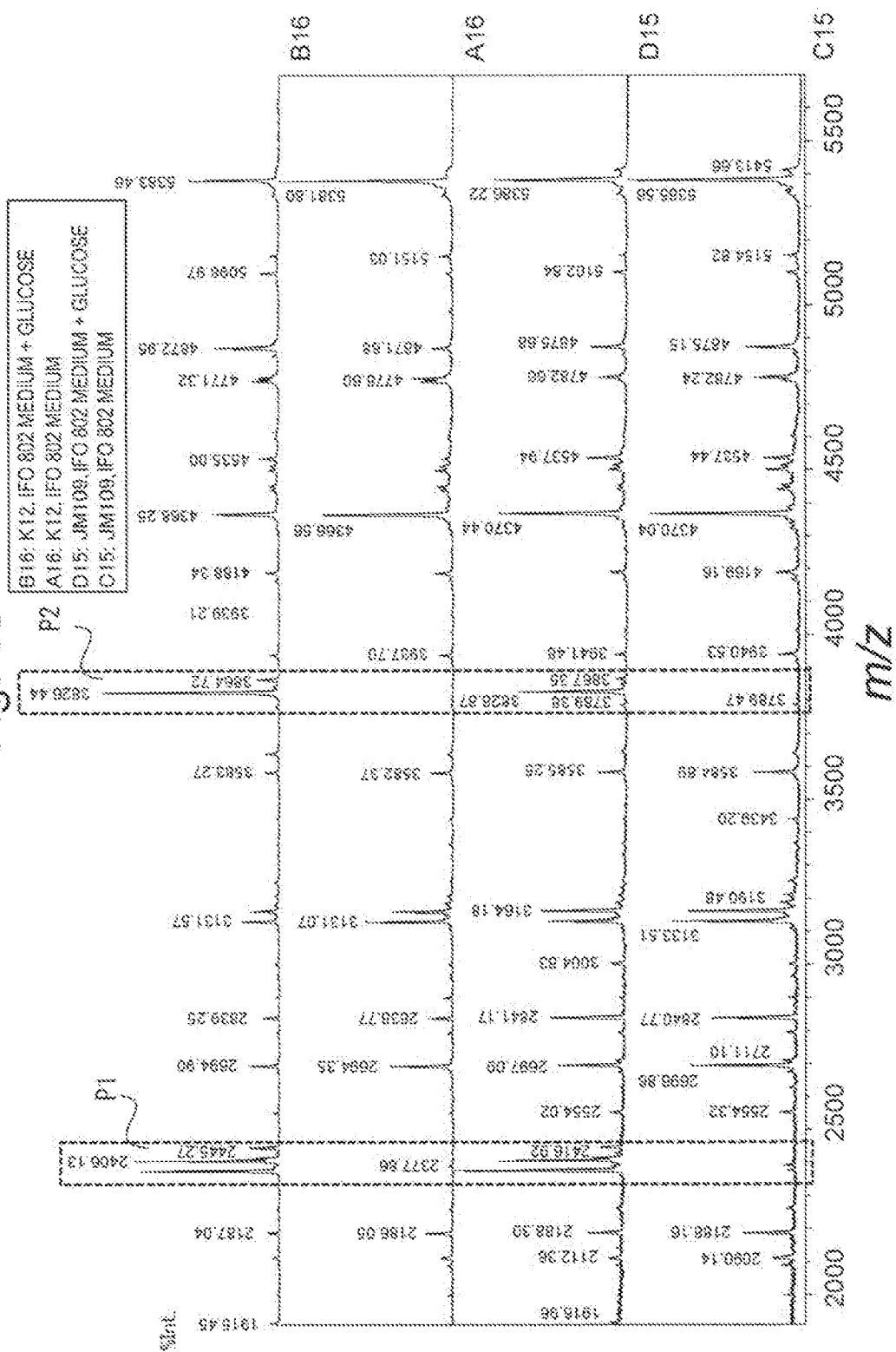

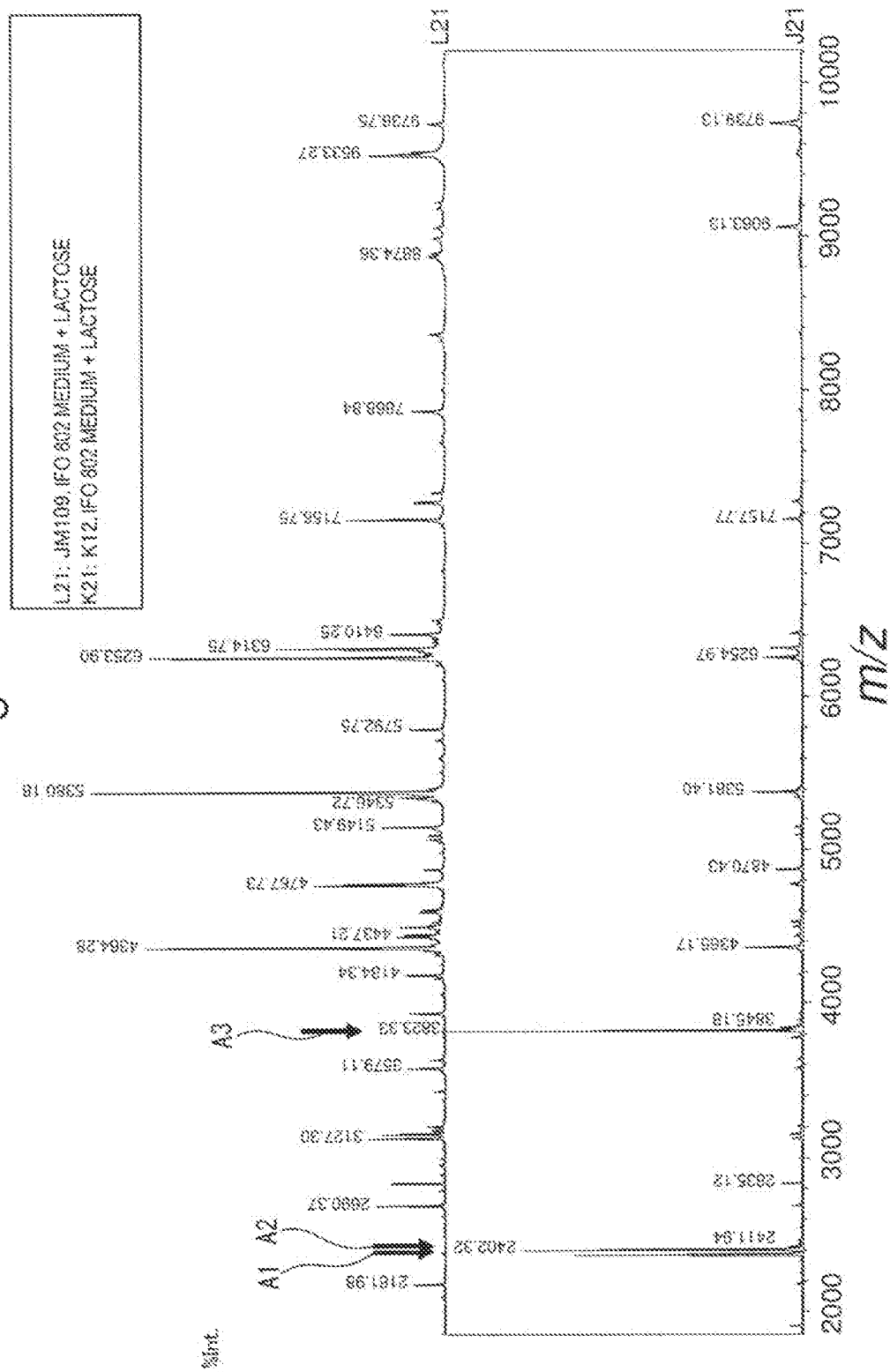

ANALYSIS METHOD, MICROORGANISM IDENTIFICATION METHOD, AND TESTING METHOD

TECHNICAL FIELD

The present invention relates to an analysis method, a microorganism identification method, and a testing method.

BACKGROUND ART

Identification of microorganisms and test of pathogenicity, drug resistance, and the like are important in medical care, research on microorganisms, and the like. It is known that there is a difference in pathogenicity and drug resistance among microorganisms of different strains of the same genus and species. For example, enterohemorrhagic *E. coli* causing food poisoning and *E. coli* present as indigenous bacteria in the intestines of healthy individuals are the same genus and species. Such identification of microorganisms of different strains of the same genus and species has been performed by a degradability test or the like in which microorganisms are cultured in the presence of a predetermined sugar, and a change in pH of the medium due to sugar decomposition is distinguished by color development.

In such a method, it is possible to make only two-alternative determinations such as presence or absence of color development, and it has been difficult to obtain detailed information on the classifications or characteristics of microorganisms. In order to obtain more detailed information, it is necessary to perform the degradability test with several kinds of sugars, and the like, which is complicated. In this regard, in Patent Literature 1, the resistance of microorganisms to an antibiotic is determined by comparing a mass spectrum obtained in mass spectrometry of the microorganisms cultured in a medium prepared by adding the antibiotic with a reference mass spectrum.

CITATION LIST

Patent Literature

Patent Literature 1: U.S. Pat. No. 8,293,496

SUMMARY OF INVENTION

Technical Problem

It has been desired that more information is provided by mass spectrometry of microorganisms cultured under different conditions.

Solution to Problem

According to a first aspect of the present invention, an analysis method includes: preparing a sample containing microorganisms; placing the microorganisms under a first condition and then performing a first mass spectrometry on a substance produced by the microorganisms; and obtaining information on characteristics or classifications of the microorganisms contained in the sample on a basis of a difference between a first data obtained in the first mass spectrometry and a second data obtained when a second mass spectrometry is performed on a substance produced by the microorganisms after having been placed under a second condition as well as a reference data in which classifications or characteristics of the microorganisms are associated with the data obtained in the mass spectrometry of the microorganisms, in which the first condition and the second condition differ in a sugar concentration or an oxygen concentration in an environment in which the microorganisms are placed.

According to a second aspect of the present invention, it is preferable that the analysis method according to the first aspect further includes performing the second mass spectrometry on the substance produced by the microorganisms after the microorganisms have been placed under the second condition.

According to a third aspect of the present invention, it is preferable that, in the analysis method according to the first or second aspect, the first condition and the second condition differ in the sugar concentration, and the sugar is at least one sugar selected from the group consisting of a monosaccharide, a disaccharide, a trisaccharide, and a tetrasaccharide.

According to a fourth aspect of the present invention, it is preferable that, in the analysis method of the third aspect, the sugar is at least one monosaccharide selected from the group consisting of allose, altrose, glucose, mannose, gulose, idose, galactose, talose, fucose, fuculose, rhamnose, psicose, fructose, sorbose, tagatose, ribose, arabinose, xylose, lyxose, ribulose, xylulose, deoxyribose, sedoheptulose, ketotetrose, erythrulose, aldotetrose, erythrose, threose, ketotriose, and aldotriose.

According to a fifth aspect of the present invention, it is preferable that, in the analysis method of the third aspect, the sugar is at least one disaccharide selected from the group consisting of sucrose, lactose, maltose, trehalose, turanose, and cellobiose.

According to a sixth aspect of the present invention, it is preferable that, in the analysis method of the third aspect, the sugar is at least one trisaccharide selected from the group consisting of raffinose, melezitose, and maltotriose.

According to a seventh aspect of the present invention, it is preferable that, in the analysis method of the third aspect, the sugar is at least one tetrasaccharide selected from the group consisting of acarbose and stachyose.

According to an eighth aspect of the present invention, it is preferable that, in the analysis method according to any one of the first to seventh aspects, the difference is presence or absence of a peak in a mass spectrum or a difference in intensity or area between peaks.

According to a ninth aspect of the present invention, it is preferable that, in the analysis method according to the eighth aspect, the peak is a peak corresponding to an acid shock protein.

According to a tenth aspect of the present invention, it is preferable that, in the analysis method according to any one of the first to ninth aspects, an analysis sample for at least one of the first mass spectrometry or the second mass spectrometry is prepared using an aqueous solution containing at least one of an acid or an organic solvent.

According to an eleventh aspect of the present invention, it is preferable that, in the analysis method of the tenth aspect, the acid is trifluoroacetic acid.

According to a twelfth aspect of the present invention, it is preferable that, in the analysis method of the tenth aspect, the organic solvent is methanol, ethanol, isopropanol, or acetonitrile.

According to a thirteenth aspect of the present invention, it is preferable that, in the analysis method according to any one of the first to twelfth aspects, in the first mass spectrometry and the second mass spectrometry, ionization is performed by matrix-assisted laser desorption/ionisation or electrospray ionization.

According to a fourteenth aspect of the present invention, it is preferable that, in the analysis method according to any one of the first to thirteenth aspects, the information includes strains of microorganisms.

According to a fifteenth aspect of the present invention, there is provided a microorganism identification method for analyzing microorganisms by the analysis method according to any one of the first to fourteenth aspects, in which the information includes classifications of microorganisms, and the microorganisms are identified on a basis of the information.

According to a sixteenth aspect of the present invention, there is provided a testing method for performing the analysis method according to any one of the first to thirteenth aspects, in which the information includes characteristics of microorganisms, and the characteristics of the microorganisms are tested on a basis of the information.

Advantageous Effects of Invention

According to the present invention, it is possible to obtain information on the classifications, characteristics, or the like of microorganisms using mass spectrometry on the basis of a difference in culture conditions or the like.

BRIEF DESCRIPTION OF DRAWINGS

FIG. 10 shows mass spectra obtained from *E. coli* K-12 strains cultured in a medium containing glucose (the first row from the top) and a medium containing no glucose (the second row from the top), respectively, and mass spectra obtained from *E. coli* JM 109 strains cultured in a medium containing glucose (the third row from the top) and a medium containing no glucose (the fourth row from the top), respectively.

FIG. 11 is a diagram showing a mass spectrum obtained from a JM 109 strain cultured in a medium containing lactose (upper row) and a mass spectrum obtained from a K-12 strain cultured in a medium containing lactose (lower row).

DESCRIPTION OF EMBODIMENTS

Figure 1:
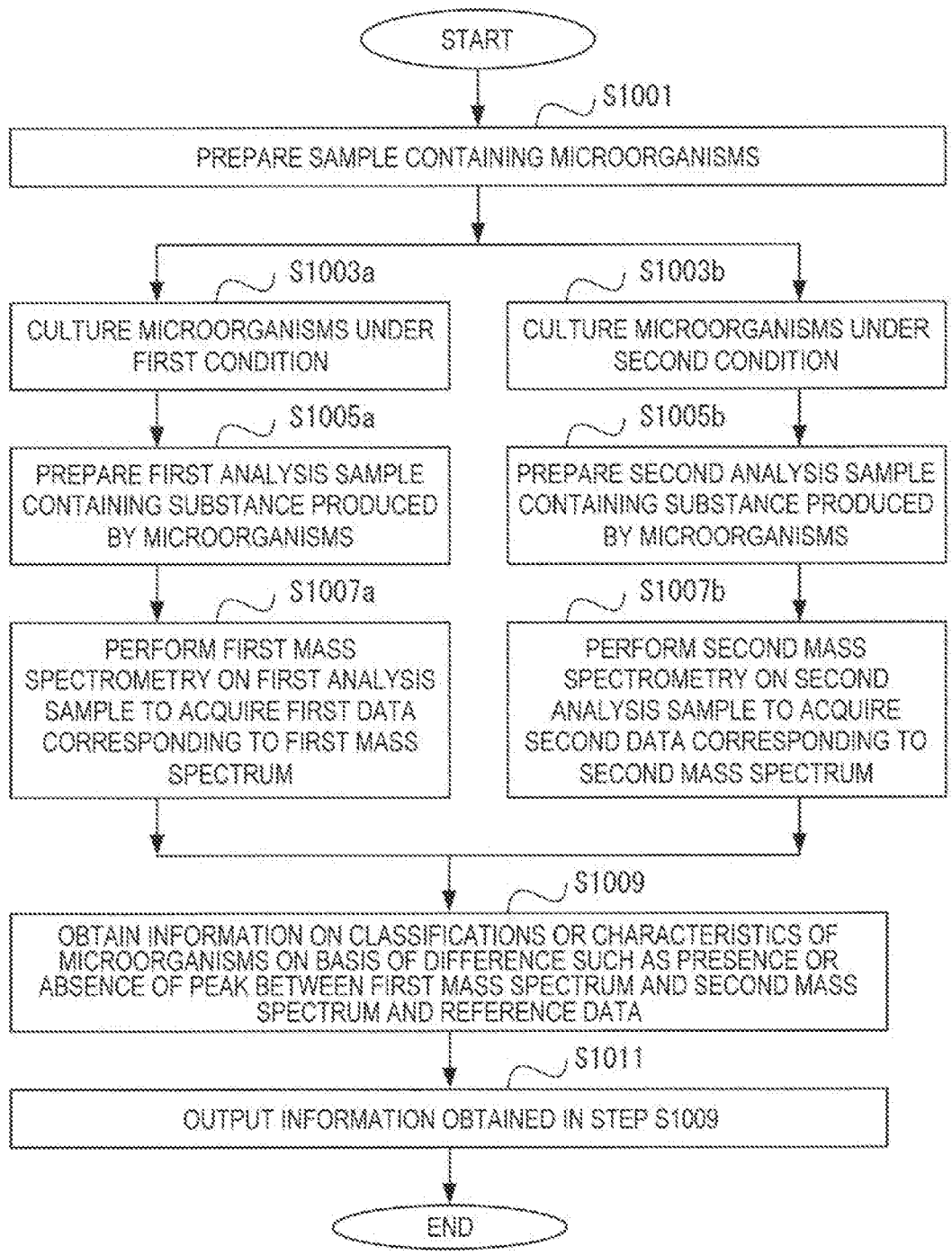
FIG. 1 is a flowchart illustrating a flow of an analysis method according to one embodiment.

Hereinafter, embodiments of the present invention will be described with reference to the drawings.

First Embodiment

The analysis method of this embodiment obtains information on characteristics or classifications of microorganisms on the basis of a difference between a data obtained in a mass spectrometry (hereinafter, referred to as first mass spectrometry) of a substance produced by the microorganisms placed under a first condition and a data obtained in a mass spectrometry (hereinafter, referred to as second mass spectrometry) of a substance produced by the microorganisms placed under a second condition.

The first condition and the second condition are different conditions. The inventors have found that when the first condition and the second condition differ in a sugar concentration, an oxygen concentration, or the like in an environment in which the microorganisms are placed, different data is obtained depending on the classifications, characteristics, or the like of the microorganisms in a first mass spectrometry and a second mass spectrometry. Therefore, it is preferable that the first condition and the second condition differ in at least one of the sugar concentration or the oxygen concentration in the environment in which the microorganisms are placed.

Concerning Sample

There is no particular limitation on the sample prepared for the analysis method of this embodiment as long as the sample contains microorganisms. As the microorganisms in the sample, it is preferable to use microorganisms in which the purity of one kind of microorganisms is increased by isolation culture or the like. For example, the sample is derived from food, medicine, or the like. Samples derived from these food and medicine can be used for inspection of quality control of food, medicine, or the like by the analysis method of this embodiment. In other examples, samples are derived from substances taken from the environment, such as drinking water or soil. The samples derived from these substances can be used for inspection as to whether the environment from which the samples are derived satisfies a predetermined standard or the like by the analysis method of this embodiment. There is no particular limitation on microorganisms contained in a sample as long as different data can be obtained depending on the classifications or characteristics of microorganisms in the first mass spectrometry and the second mass spectrometry. The microorganisms are preferably eubacteria, and more preferably *E. coli*, *Acinetobacter*, or *Enterobacter*.

Concerning Culture under First Condition and Second Condition

The microorganisms contained in a sample is divided into at least two and cultured under the first condition and the second condition, respectively. In the first condition and the second condition, the medium for culturing the microorganisms may be a solid medium such as an agar medium or a liquid medium. There is no particular limitation on the basic composition of the medium, and it is possible to use a known medium such as IFO 802 medium (composition of aqueous solution: 1 mass % of hipolypepton, 0.2 mass % of yeast extract, 0.1 mass % of $MgSO_4 \cdot 7H_2O$, pH 7.0).

There is no particular limitation on a difference between the first condition and the second condition as long as a difference occurs between the data obtained in the first mass spectrometry and the data obtained in the second mass spectrometry, and the information on the classifications or characteristics of microorganisms is obtained on the basis of the difference. Preferably, the first condition and the second condition differ in the sugar concentration in the medium for culturing the microorganisms, or differ in the oxygen concentration in the gas in contact with the microorganisms. The first condition and the second condition may differ in both the sugar concentration and the oxygen concentration.

In a case where the first condition and the second condition differ in the sugar concentration in the medium, there is no particular limitation on the sugar concentration in the first condition and the second condition as long as information on the microorganisms or characteristics can be obtained on the basis of the difference in the obtained data. In order to obtain a clearer result, it is preferable that sugar is not added to the medium under one of the first condition and the second condition, and sugar is added to the medium at an appropriate concentration such as 0.1% or more and 10% or less under the other condition.

In the first condition and the second condition, there is no particular limitation on the type of the sugar contained in the medium at different concentrations, and a monosaccharide, a disaccharide, a trisaccharide, and a tetrasaccharide are preferable.

In a case where the sugar contained in the medium is a monosaccharide, the monosaccharide is preferably allose, altrose, glucose, mannose, gulose, idose, galactose, talose, fucose, fuculose, rhamnose, psicose (also referred to as allulose), fructose, sorbose, tagatose, ribose, arabinose, xylose, lyxose, ribulose, xylulose, deoxyribose, sedoheptulose, ketotetrose, aldotetrose, ketotriose (dihydroxyacetone), or aldotriose (glyceraldehyde). As ketotetrose, erythrulose is preferable. As aldotetrose, erythrose or threose is preferable. A plurality of kinds of these monosaccharides may be used in combination. The sugar is more preferably glucose.

In a case where the sugar contained in the medium is preferably at least one disaccharide selected from the group consisting of sucrose, lactose, maltose, trehalose, turanose, and cellobiose. The sugar is more preferably lactose.

In a case where the sugar contained in the medium is a trisaccharide, the trisaccharide is preferably at least one trisaccharide selected from the group consisting of raffinose, melezitose, and maltotriose.

In a case where the sugar contained in the medium is a tetrasaccharide, the tetrasaccharide is preferably at least one tetrasaccharide selected from the group consisting of acarbose and stachyose.

The sugar contained in the medium may be a monosaccharide, disaccharide, trisaccharide, or tetrasaccharide compound other than those listed above, or a sugar obtained by binding five or more monosaccharides.

In a case where the oxygen concentration of the gas in contact with the microorganisms is made varied between the first condition and the second condition, there is no particular limitation on the value of the oxygen concentration in the first condition and the second condition as long as the information on the classifications or characteristics of microorganisms can be obtained on the basis of the difference in the obtained data. The difference in the oxygen concentration between the first condition and the second condition is preferably 10% or more, and more preferably 15% or more. As a preferred example, air is used as the ambient atmosphere of the microorganisms under one of the first and second conditions, and the oxygen concentration can be reduced by disposing the microorganisms, a medium, and an oxygen absorbent in a sealed container or the like under the other condition. In this case, the reduced oxygen concentration is preferably 5% or less, and more preferably 1% or less. As the oxygen absorbent, an oxygen absorbent contained in a known product such as AnaeroPack (registered trademark) can be used.

There is no particular limitation on the temperature of the medium at the time of culture, and the temperature is preferably 25° C. to 40° C., and more preferably 37° C. It is possible to select a temperature suitable for the growth of microorganisms as appropriate. The culture time may be appropriately determined on the basis of the growth rate of microorganisms or the like determined according to the selected culture conditions, and is preferably 12 hours to 36 hours, and can be set to, for example, 18 hours. In the case of analyzing microorganisms by mass spectrometry, a time for accumulating molecules necessary for color development or the like is not required as compared with a conventional degradability test or the like, and thus culture can be performed in a short time.

Concerning Preparation of Analysis Sample

Upon completion of the culture under each of the first condition and the second condition, analysis samples for a first mass spectrometry and a second mass spectrometry are prepared. In the case of performing mass spectrometry using matrix-assisted laser desorption/ionisation (hereinafter, referred to as MALDI), microorganisms obtained by culture are recovered, a solution containing a matrix (hereinafter, referred to as a matrix solution) is added to each of the obtained samples, and the mixture is dropped onto a sample plate for MALDI and dried. The matrix solution may be added after the sample is placed on the sample plate for MALDI. There is no particular limitation on the type of the matrix, and it is possible to use α-cyano-4 hydroxycinnamic acid (CHCA), sinapinic acid, or the like. It is possible to prepare the solvent of the matrix solution using at least one of an acid and an organic solvent. Preferably, methanol, ethanol, isopropanol, or acetonitrile is used as the organic solvent. It is possible to use, as the solvent, for example, a solvent obtained by adding 0 to 3 vol % of trifluoroacetic acid (TFA) to an aqueous solution containing several tens of vol % of an organic solvent such as acetonitrile.

After extracting the proteins from the microorganisms obtained by culture, a matrix solution may be added to the extract to prepare an analysis sample. Even when mass spectrometry is performed without using MALDI, it is possible to prepare an analysis sample by a known method or the like according to the ionization method and the type of mass spectrometer as appropriate.

First Mass Spectrometry and Second Mass Spectrometry

The ionization method in the first mass spectrometry and the second mass spectrometry preferably uses MALDI because monovalent ions are easily generated and analysis is easy. Further, time-of-flight mass spectrometry is preferable to accurately detect molecules with a high mass such as several kDa or more. Time-Of-Flight mass spectrometry using MALDI (hereinafter, referred to as MALDI-TOFMS) is particularly preferable because it combines the advantages of MALDI and time-of-flight mass spectrometry. However, there is no particular limitation on the methods of the first mass spectrometry and the second mass spectrometry as long as the information on the classifications or characteristics of microorganisms can be obtained on the basis of a difference between the data obtained in the first mass spectrometry (hereinafter, referred to as first data) and the data obtained in the second mass spectrometry (hereinafter, referred to as second data). For example, any ionization method such as an electrospray method can be used. Further, a mass analyzer such as a quadrupole mass filter or an ion trap can be used, and multistage mass spectrometry may be performed using a combination of a plurality of arbitrary mass analyzers, in addition to a single mass spectrometer. In the first mass spectrometry and the second mass spectrometry, a data corresponding to a mass spectrum obtained by detection of an ionized sample is generated. The mass spectrum obtained by the first mass spectrometry and the mass spectrum obtained by the second mass spectrometry are referred to as a first mass spectrum and a second mass spectrum, respectively.

Concerning Data Analysis

There is no particular limitation on the method of data analysis as long as the information on the classifications or characteristics of microorganisms can be obtained on the basis of the difference between the first data and the second data. Preferably, the data analysis is performed on the basis of the presence or absence of predetermined peaks in the first mass spectrum and the second mass spectrum or a difference in the magnitude between the peaks. It is possible to perform the data analysis using an arbitrary data analyzer, for example, an information-processing device such as a personal computer, or a processing device in a mass spectrometer.

In a case where the sugar concentration in the medium is changed under the first condition and the second condition, it is possible to perform the following data analysis. It is assumed that the medium contains sugar under the first condition, and the medium contains no sugar under the second condition. At this time, a peak that does not appear in the second mass spectrum but appears in the first mass spectrum (hereinafter, referred to as a specific peak) is identified. In order to remove noise and unnoticeable peaks, it is possible to extract, for example, specific peaks having a relative intensity or a relative peak area greater than or equal to a certain level with respect to an arbitrary base peak.

Meanwhile, there is previously acquired m/z of a peak (hereinafter, referred to as a reference peak) that is detected in the case of adding sugar to a medium and is not detected in the case of adding no sugar to the medium, in the classifications of strains of microorganisms or the like obtained from past measurement data, theoretical values, or the like. Hereinafter, a data in which the classifications or characteristics of microorganisms are associated with the reference peak, i.e., a data obtained in mass spectrometry of the microorganisms, is referred to as a reference data. The data analyzer used for data analysis in the analysis method of this embodiment includes a storage medium that stores the reference data as a database, or is configured to be able to refer to the reference data from the storage medium via communication.

It is determined whether m/z of a specific peak and m/z of a reference peak are within an error range on the basis of the accuracy of the first mass spectrometry and the second mass spectrometry. When it is determined to be within the error range, the specific peak and the reference peak are associated with each other. When it is determined not to be within the error range, the specific peak and the reference peak are not associated with each other. When all of the reference peaks in a certain strain of microorganisms or the like are associated with the specific peak, the microorganisms contained in the sample can be identified as the strain of microorganisms or the like. Alternatively, the probability that the microorganisms contained in the sample are the microorganisms corresponding to the reference peak may be calculated on the basis of the number of specific peaks associated with the reference peak. Such classifications of microorganisms can be performed for different strains of the same genus and species, or may be performed for classification other than strains such as genera and species.

As described above, the reference peak and the specific peak are associated with each other on the basis of the presence or absence of the specific peak corresponding to m/z of the reference peak, and further the association may be performed on the basis of a quantitative numerical value such as intensity or area of a peak. The same applies to the following.

As described above, there is provided a microorganism identification method for acquiring information on the classifications of microorganisms contained in a sample using the analysis method of this embodiment.

A data in which the characteristics of microorganisms such as pathogenicity or drug resistance are associated with the reference peak may be used as the reference data. The characteristics of microorganisms are characteristics of microorganisms such as sugar assimilability and optimum growth temperature, or pathogenicity and drug resistance, and can include, for example, different characteristics within the classifications of microorganisms. In this case, for example, when all of the reference peaks commonly possessed by microorganisms having specific characteristics are associated with specific peaks, it is possible to obtain information that the microorganisms contained in the sample have the characteristics. Alternatively, the probability may be calculated as described above. There is no particular limitation on the pathogenicity to be analyzed as long as the data analysis can be performed on the basis of the difference between the first data and the second data. The pathogenicity, is for example, enterohemorrhagic *Escherichia coli* infection. Similarly, there is no particular limitation on the drug resistance to be analyzed, and it is, for example, antibacterial resistance.

As described above, there is provided a testing method in which the information on the characteristics of microorganisms contained in a sample is acquired using the analysis method of this embodiment, and the characteristics of the microorganisms are tested on the basis of the information.

During the culture under the first condition and the second condition, even in the case of changing the oxygen concentration of the gas in contact with the microorganisms, it is possible to perform the same data analysis. In the first condition, the oxygen concentration is a low oxygen concentration such as 5% or less. In second condition, the oxygen concentration is close to air such as 18% or more and 22% or less. At this time, a peak that does not appear in the second mass spectrum but appears in the first mass spectrum is set as a specific peak. On the basis of the past measurement data, theoretical values, or the like, a peak detected when the microorganisms are cultured at a low oxygen concentration and not detected when the microorganisms are cultured at an oxygen concentration close to air is used as a reference peak. Even in this case, similarly to the case where the sugar concentration is changed, it is possible to acquire the information on the classifications or characteristics of microorganisms on the basis of the association between the specific peak and the reference peak.

FIG. 1 is a flowchart illustrating a flow of an analysis method of this embodiment. In step S1001, a sample containing microorganisms is prepared. Upon completion of step S1001, both step S1003a and step S1003b start.

In step S1003a, the microorganisms are cultured under a first condition. Upon completion of step S1003a, step S1005a starts. In step S1005a, an analysis sample containing a substance produced by the microorganisms placed under the first condition (hereinafter, referred to as a first analysis sample) is prepared. Upon completion of step S1005a, step S1007a starts. In step S1007a, a first mass spectrometry is performed on the first analysis sample to acquire a first data corresponding to a first mass spectrum.

In step S1003b, the microorganisms are cultured under a second condition. Upon completion of step S1003b, step S1005b starts. In step S1005b, an analysis sample containing a substance produced by the microorganisms placed under the second condition (hereinafter, referred to as a second analysis sample) is prepared. Upon completion of step S1005b, step S1007b starts. In step S1007b, a second mass spectrometry is performed on the second analysis sample, and a data analyzer acquires a second data corresponding to a second mass spectrum. Upon completion of step S1007a and step S1007b, step S1009 starts.

In step S1009, the information on the classifications or characteristics of microorganisms is obtained on the basis of a difference such as the presence or absence of a peak between the first mass spectrum and the second mass spectrum and the reference data. For example, reference peaks associated with the specific peaks obtained by the first and second mass spectrometries are retrieved from the database. Upon completion of step S1009, step S1011 starts. In step S1011, the information obtained in step S1009 is output. A display monitor connected to the data analyzer displays the information, or a printer or the like prints and outputs the information.

Figure 2:
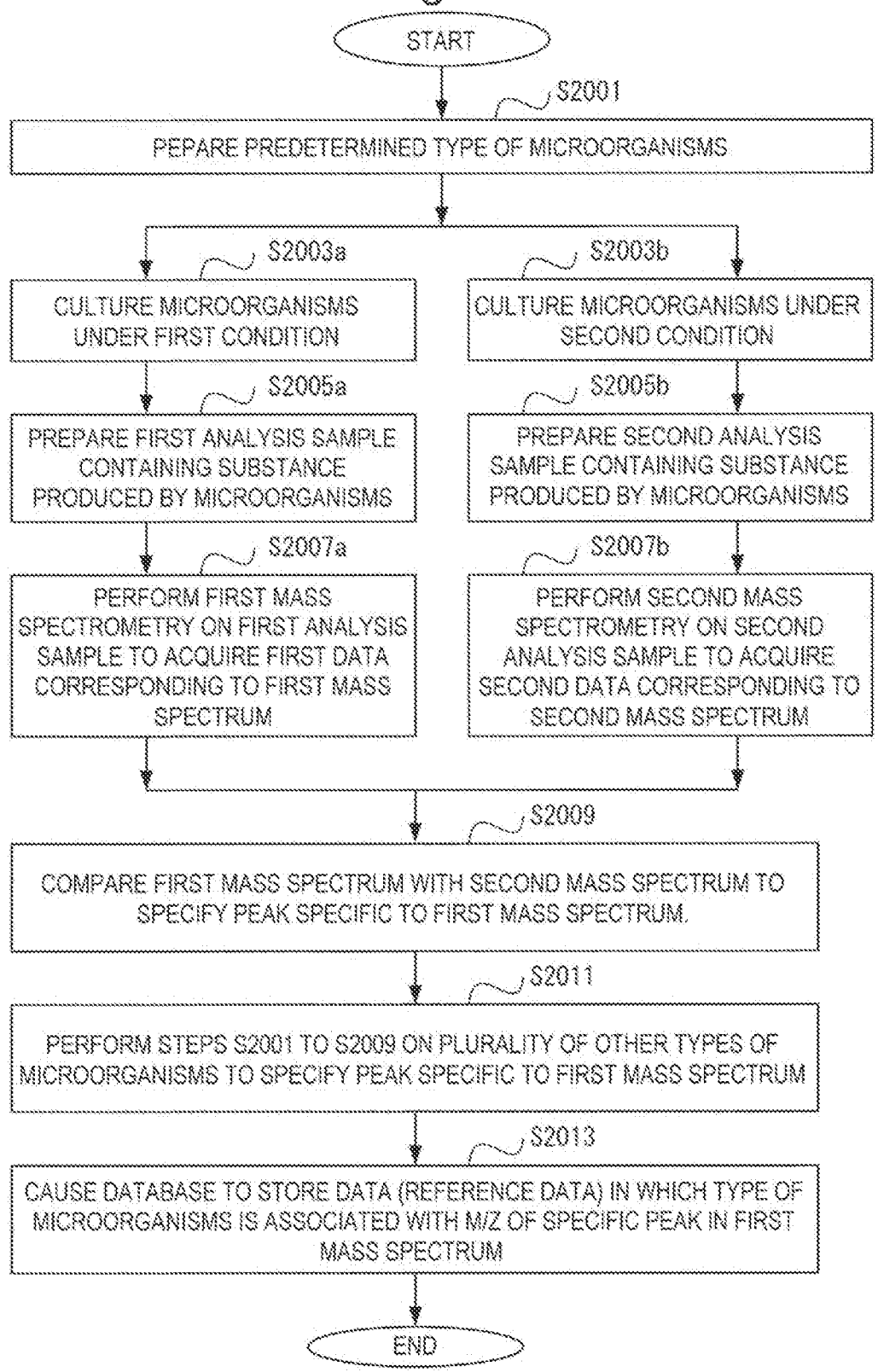
FIG. 2 is a flowchart illustrating a flow of an analysis method according to one embodiment.

FIG. 2 is a flowchart illustrating a flow of creating a database including a reference data from the data obtained in the first mass spectrometry and the second mass spectrometry in the analysis method of this embodiment. In practice, before performing the analysis method shown in FIG. 1, the database of the reference data is created in advance by the method shown in FIG. 2. Although FIG. 2 illustrates an example in which a specific peak of the first mass spectrum is recorded in the database as the reference data, the same process may be performed on the second mass spectrum.

In step S2001, a sample containing a predetermined type of microorganisms is prepared. The type of microorganisms may be known, or may be identified by a known method or the like before step S2013. Upon completion of step S2001, both step S2003a and step S2003b start. Steps S2003a to S2007a and steps S2003b to S2007b are the same as steps S1003a to S1007a and steps S1003b to S1007b in the flowchart of FIG. 1, respectively, and thus the description of these steps is omitted. Upon completion of step S2007a and step S2007b, step S2009 starts.

In step S2009, the first mass spectrum is compared with the second mass spectrum to specify a peak specific to the first mass spectrum. Upon completion of step S2009, step S2011 starts. In step S2011, steps S2001 to S2009 are also performed on a plurality of other types of microorganisms to specify a peak specific to the first mass spectrum. Upon completion of step S2011, step S2013 starts.

In step S2013, the database stores a data (reference data) in which the type of microorganisms is associated with m/z of the specific peak in the first mass spectrum. Upon completion of step S2013, the database construction processing ends.

When a peak specific to a certain microorganism is specified in step S2009 or step S2011, the reference data corresponding to the database may be sequentially stored as in step S2013.

One Example of Specific Peak

The inventors have identified peaks corresponding to m/z 2371, 2401, and 3823, respectively, as specific peaks observed in the first mass spectrum under the first condition that microorganisms (*E. coli* K-12 strain) were cultured in a medium containing sugar and under the second condition that microorganisms (*E. coli* K-12 strain) were cultured in a medium containing no sugar. Further, the inventors have identified the molecules corresponding these peaks by tandem mass spectrometry (see Second Example described later).

The specific peaks corresponded to molecules constituting a part of the acid shock protein (UniProt accession number: P 36560) of the *E. coli* K-12 strain. The amino acid sequence of the acid shock protein of the *E. coli* K-12 strain is "MKKVLALVVA AAMGLSSAAF AAETTTTPAP TATTTKAAPA KTTHHKKQHK AAPAQKAQAA KKHHKNTKAE QKAPEQKAQA AKKHAKKHSH QQPAKPAAQP AA" (SEQ ID NO: 1). The specific peak corresponding to m/z 3823 (see FIG. 4) was a molecule corresponding to the 22nd to 58th amino acids in the amino acid sequence of the acid shock protein. The specific peak corresponding to m/z 2371 was a molecule corresponding to the 59th to 79th amino acids in the amino acid sequence of the acid shock protein. The specific peak corresponding to m/z 2401 was a molecule corresponding to the 80th to 102nd amino acids in the amino acid sequence of the acid shock protein.

There are also other genera of microorganisms expressing proteins corresponding to the acid shock protein. For example, Group D: *Shigella sonnei* includes a gene encoding the acid shock protein (UniProt accession number: A0A236HJK2) having an amino acid sequence different from that of the acid shock protein of *E. coli* K-12 strain. Therefore, it has been estimated that the analysis method of this embodiment can be preferably applied to various microorganisms expressing at least the acid shock protein. The environment in which the microorganisms are placed becomes acidic due to a difference in the sugar concentration, the oxygen concentration, or the like between the first condition and the second condition, as a result of which the acid shock protein is expressed, and a specific peak can be acquired. Consequently, in the analysis method of this embodiment, it is possible to make the environment in which the microorganisms are placed acidic under either the first condition or the second condition.

The above-described acid shock protein is one example of a molecule that is specifically expressed under one of the first condition and the second condition when the sugar concentration or the oxygen concentration is made varied between the first and second conditions. The present invention does not limit only the peak corresponding to the acid shock protein as a specific peak. There is a difference between the first data and the second data when varying the sugar concentration, the oxygen concentration, or the like. There is no particular limitation on the molecule or the like that causes the difference as long as the information on the classifications or characteristics of microorganisms can be obtained on the basis of the difference.

According to the above-described embodiment, the following effects can be obtained.

(1) An analysis method of this embodiment includes: placing microorganisms under a first condition and then performing a first mass spectrometry on a substance produced by the microorganisms; placing microorganisms under a second condition and then performing a second mass spectrometry on a substance produced by the microorganisms; and obtaining information on characteristics or classifications of the microorganisms on a basis of a difference between a first data obtained in the first mass spectrometry and a second data obtained in the second mass spectrometry as well as a reference data in which classifications or characteristics of the microorganisms are associated with the data obtained in the mass spectrometry of the microorganisms, in which the first condition and the second condition differ in a sugar concentration or an oxygen concentration in an environment in which the microorganisms are placed. As a result, it is possible to obtain information on the classifications, characteristics, or the like of microorganisms by mass spectrometry on the basis of a difference in culture conditions or the like.

(2) In the analysis method of this embodiment, the difference is presence or absence of a specific peak in a mass spectrum or a difference in intensity or area between peaks. Accordingly, it is possible to perform more detailed analysis using a mass spectrum including quantitative information of various molecules.

(3) In the analysis method of this embodiment, the specific peak includes a peak corresponding to an acid shock protein. Accordingly, it is possible to perform analysis using variations depending on the species and strains of the acid shock protein.

The following modification is also within the scope of the present invention and can be combined with the above-described embodiment. In the following modified example, description of the same parts as those of the above-described embodiment will be omitted as appropriate.

FIRST MODIFIED EXAMPLE

In the above-described embodiment, both the first mass spectrometry and the second mass spectrometry were performed to acquire a data corresponding to each of them. However, only one of the first mass spectrometry and the second mass spectrometry may be performed, and information obtained in the past may be used for the other.

In the following description, the first mass spectrometry is performed, and the information acquired in the past is used for the second data that should be obtained in the second mass spectrometry. This modified example is useful particularly in a case where the second condition is more basic or versatile than the first condition, but is not particularly limited. For example, in a case where the first condition is to indicate a condition to culture microorganisms in a medium containing sugar and the second condition is to indicate a condition to culture microorganisms in a medium containing no sugar, the second data can be a data including the second mass spectrum or the m/z value of the peak appearing in the second mass spectrum. Thus, it is possible to identify a specific peak in a first spectrum on the basis of the first mass spectrum and the second data. When a specific peak based on the presence or absence of sugar in the medium is obtained, the specific peak is associated with the reference data based on the presence or absence of sugar, and the information on the classifications or characteristics of microorganisms can be obtained.

Figure 3:
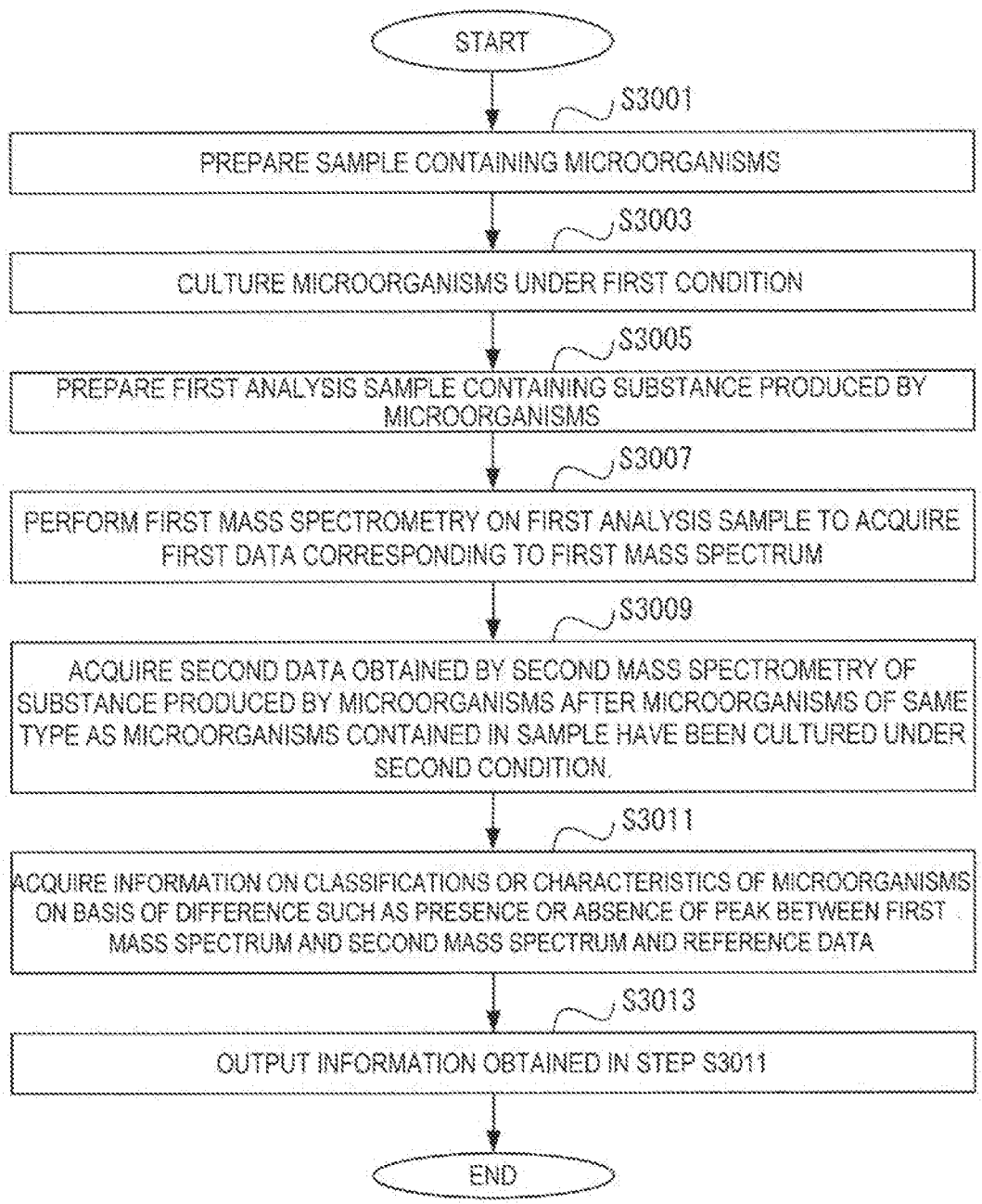
FIG. 3 is a flowchart illustrating a flow of an analysis method according to one embodiment.

FIG. 3 is a flowchart illustrating a flow of an analysis method of this embodiment. Since steps S3001 to S3007 are the same as steps S1001 and S1003a to S1007a in the flowchart of FIG. 1 described above, the description of these steps is omitted. Upon completion of step S3007, step S3009 starts.

In step S3009, the data analyzer acquires the second data obtained by the second mass spectrometry of the substance produced by the microorganisms after the microorganisms of the same type as the microorganisms contained in the sample have been cultured under the second condition. Upon completion of step S3009, step S3011 starts. Since steps S3011 and S3013 are the same as steps S1009 and S1011 of the flowchart of FIG. 1 described above, the description of these steps is omitted. Upon completion of step S3013, the process ends.

The analysis method of this modified example includes: placing microorganisms under a first condition and then performing a first mass spectrometry on the microorganisms; and obtaining information on classifications or characteristics of the microorganisms contained in a sample on a basis of a difference between a first data obtained in the first mass spectrometry and a second data obtained when a second mass spectrometry is performed on a substance produced by the microorganisms after having been placed under a second condition as well as a reference data, in which the first condition and the second condition differ in a sugar concentration or an oxygen concentration in an environment in which the microorganisms are placed. Consequently, it is possible to reduce the number of times of mass spectrometry and perform analysis more efficiently.

The present invention is not limited to the contents of the above embodiments. Other aspects conceivable within the scope of the technical idea of the present invention are also included in the scope of the present invention.

EXAMPLE

Hereinafter, Examples according to this embodiment will be described, but the present invention is not limited to the numerical values, the conditions of the device, and the like of the following Examples.

First Example

In First Example, a difference between the first condition and the second condition was defined as the presence or absence of sugar in a medium, and *E. coli* of two different strains was identified using specific peaks.

Concerning Sample

As samples, an *E. coli* K-12 strain and an *E. coli* environmental isolate were prepared. The *E. coli* environmental isolate was collected from a general environment, and applied to a solid medium to obtain an isolate. Then, the isolate was identified as *E. coli* by a microorganism identification method using MALDI. The *E. coli* K-12 strain and the *E. coli* environmental isolate were the same genus and species, and could not be identified by a conventional biochemical characterization test.

Culture and Mass Spectrometry of *E. coli* K-12 Strain

The *E. coli* K-12 strain was divided into two. One of the strains was cultured in a medium prepared by adding glucose (0.5 mass %) to an IFO 802 medium and the other strain was cultured in an IFO 802 medium, under conditions of 37° C. and 18 hours. The cultured microorganisms were centrifuged, the supernatants were discarded, and a trifluoroacetic acid-acetonitrile aqueous solution was added to the remaining bacterial cells to suspend them. The suspended solutions were centrifuged, and the supernatants were collected. The collected supernatants were diluted with an acetonitrile aqueous solution, dropped on a plate for MALDI mass spectrometry, and dried. CHCA as a matrix was added to the dried samples, and the resulting samples were dried again and subjected to time-of-flight mass spectrometry using the MALDI mass spectrometer (AXIMA Performance, manufactured by Shimadzu Corporation).

Figure 4:
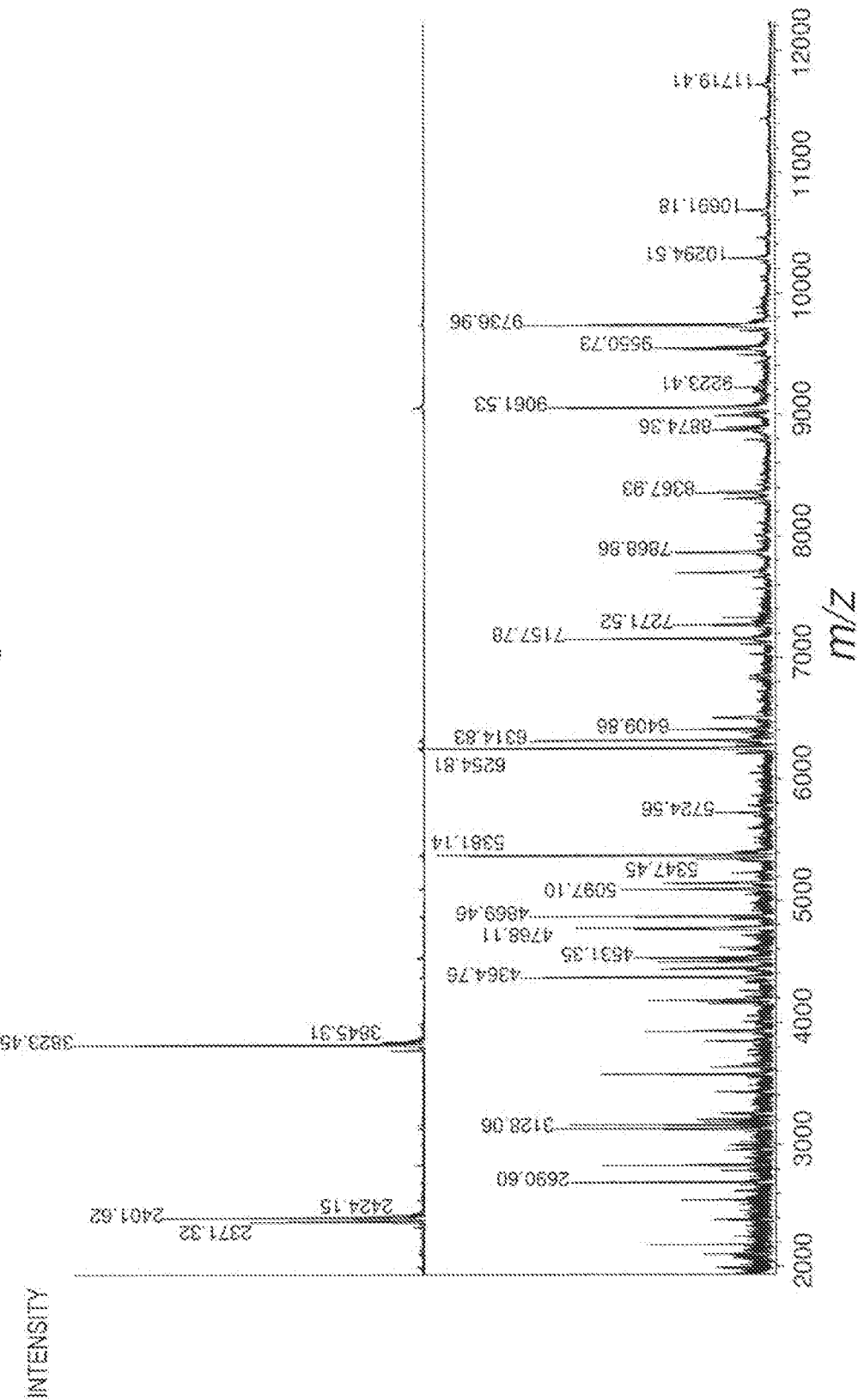
FIG. 4 shows mass spectra obtained by culturing *E. coli* K-12 strains in a medium containing glucose (upper row) and a medium containing no glucose (lower row), respectively, and performing mass spectrometry on substances produced by the bacteria.

FIG. 4 is a diagram showing a mass spectrum obtained from a K-12 strain cultured in a medium obtained by adding glucose (upper row) and a mass spectrum obtained from a K-12 strain cultured in a medium obtained by adding no glucose (lower row). In a case where the *E. coli* K-12 strain was cultured in the medium obtained by adding glucose, specific peaks at m/z 2371, m/z 2401, and m/z 3823 were observed in the obtained mass spectrum in comparison with the case of culturing in the medium obtained by adding no glucose.

Culture and Mass Spectrometry of *E. coli* Environmental Isolate

The *E. coli* environmental isolate was divided into two. One of the strains was cultured in a medium prepared by adding glucose (0.5 mass %) to an IFO 802 medium and the other strain was cultured in an IFO 802 medium, under conditions of 37° C. and 18 hours. The microorganisms after the culture were subjected to mass spectrometry in a similar manner to the above-described method for *E. coli* K-12 strain.

Figure 5:
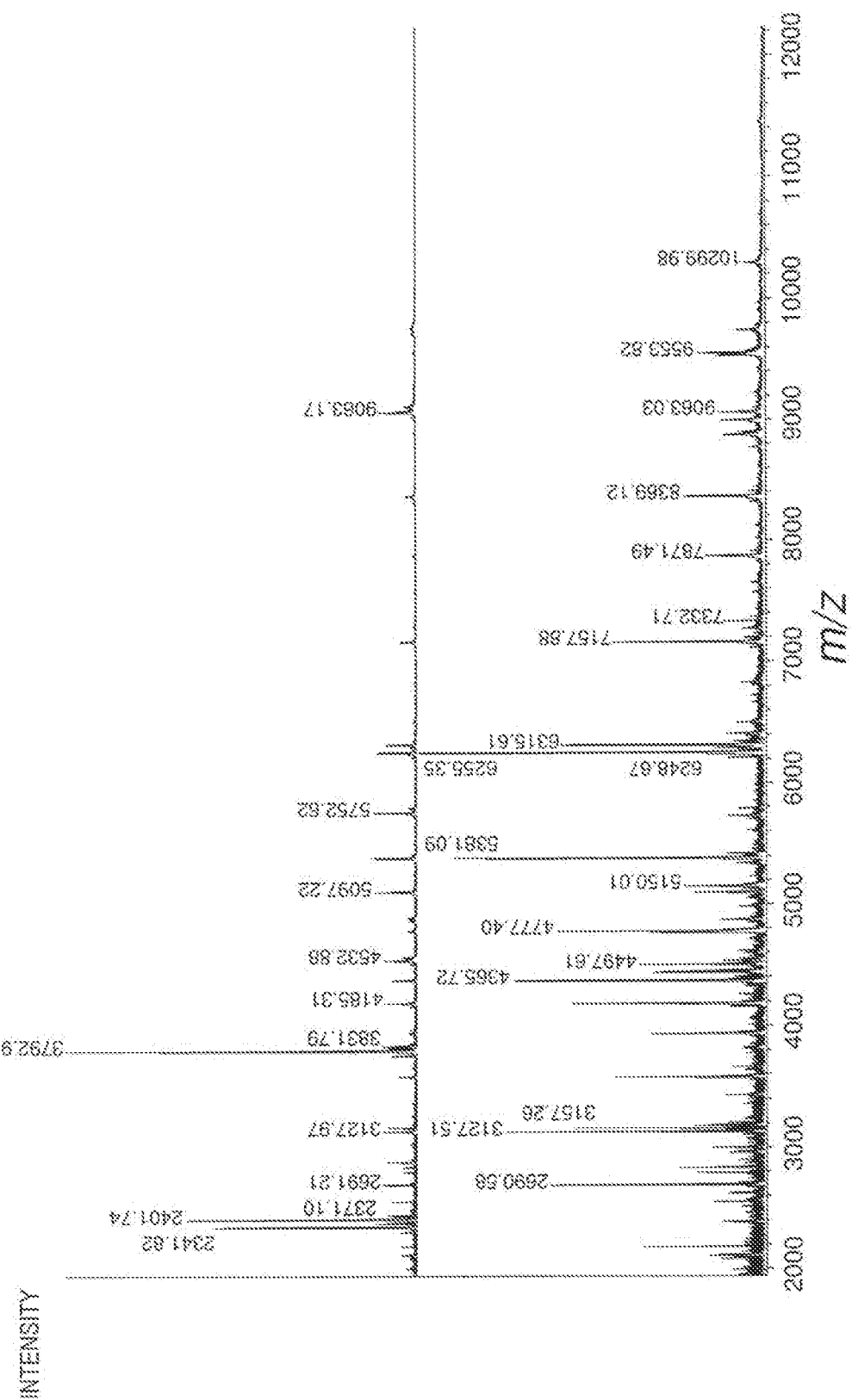
FIG. 5 shows mass spectra obtained by culturing *E. coli* environmental isolates in a medium containing glucose (upper row) and a medium containing no glucose (lower row), respectively, and performing mass spectrometry on substances produced by the bacteria.

FIG. 5 is a diagram showing a mass spectrum obtained from an environmental isolate cultured in a medium obtained by adding glucose (upper row) and a mass spectrum obtained from an environmental isolate cultured in a medium obtained by adding no glucose (lower row). In a case where the *E. coli* environmental isolate was cultured in the medium obtained by adding glucose, specific peaks at m/z 2341, m/z 2401, and m/z 3792 were observed in the obtained mass spectrum in comparison with the case of culturing in the medium obtained by adding no glucose.

Figure 6:
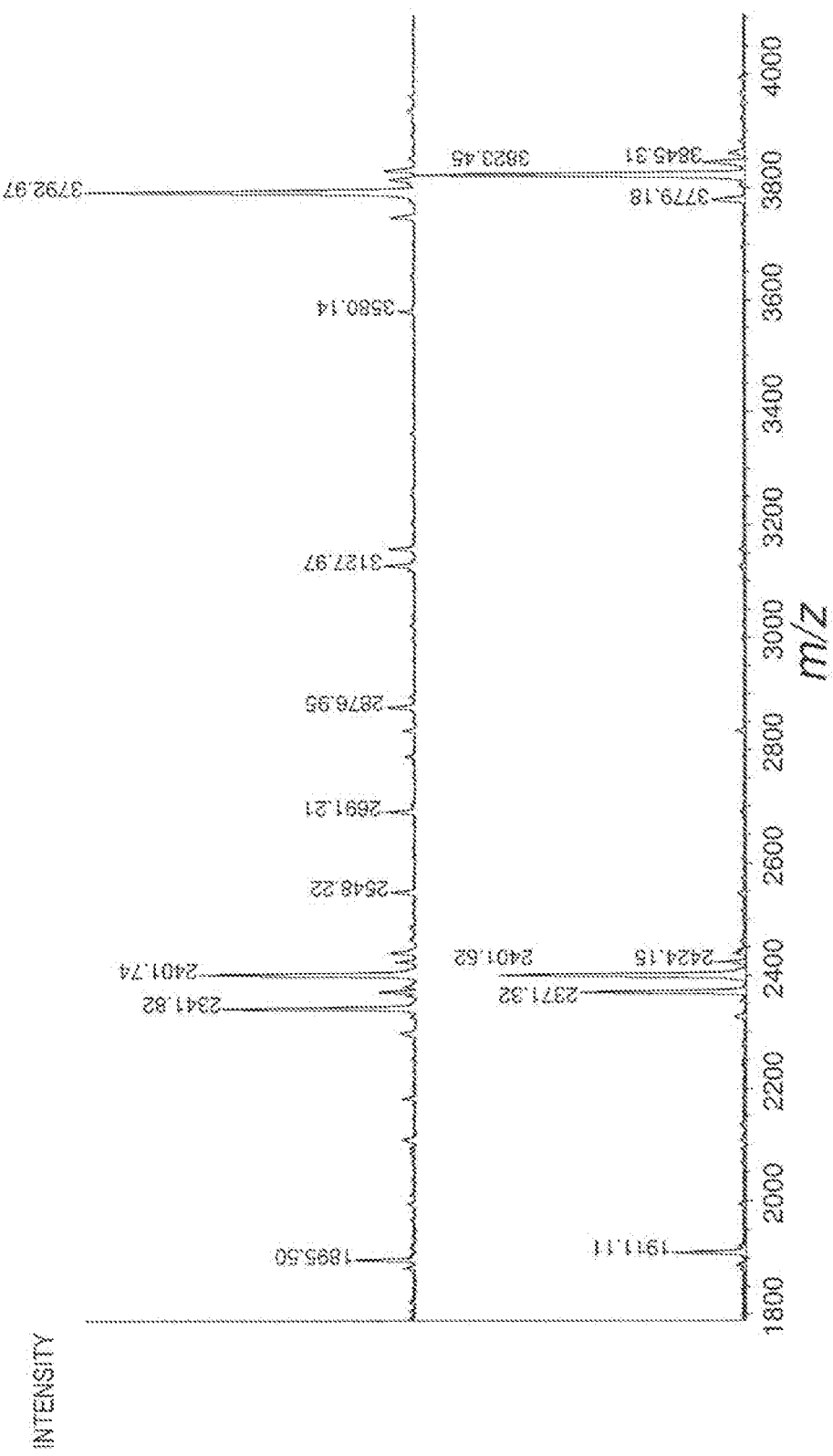
FIG. 6 shows mass spectra obtained by culturing an *E. coli* environmental isolate (upper row) and a K-12 strain (lower row) in a medium containing glucose, respectively, and performing mass spectrometry on substances produced by the bacteria.

FIG. 6 is a diagram showing a mass spectrum obtained from an *E. coli* environmental isolate cultured in a medium obtained by adding glucose (upper row) and a mass spectrum obtained from an *E. coli* K-12 strain cultured in a medium obtained by adding glucose (lower row). The two mass spectra in FIG. 6 are partially enlarged mass spectra in FIGS. 4 and 5. It can be seen that the peaks at m/z 2341, m/z 2401, and m/z 3792 are remarkable specific peaks of the *E. coli* environmental isolates. Further, it is found that the peaks at m/z 2371, m/z 2401, and m/z 3823 are remarkable specific peaks of the *E. coli* K-12 strain. As described above, it was possible to identify different strains on the basis of the characteristics that substances produced when cultured in a medium containing sugar were different.

Second Example

In a mass spectrum obtained by culturing an *E. coli* K-12 strain in a medium obtained by adding glucose and then performing mass spectrometry, a molecule corresponding to m/z 3823 observed as a specific peak was ionized by MALDI and subjected to tandem mass spectrometry. Data analysis was performed assuming that each peak in the product ion spectrum obtained by tandem mass spectrometry corresponded to a peptide fragment, and the amino acid sequence of the molecule was derived.

Figure 7:
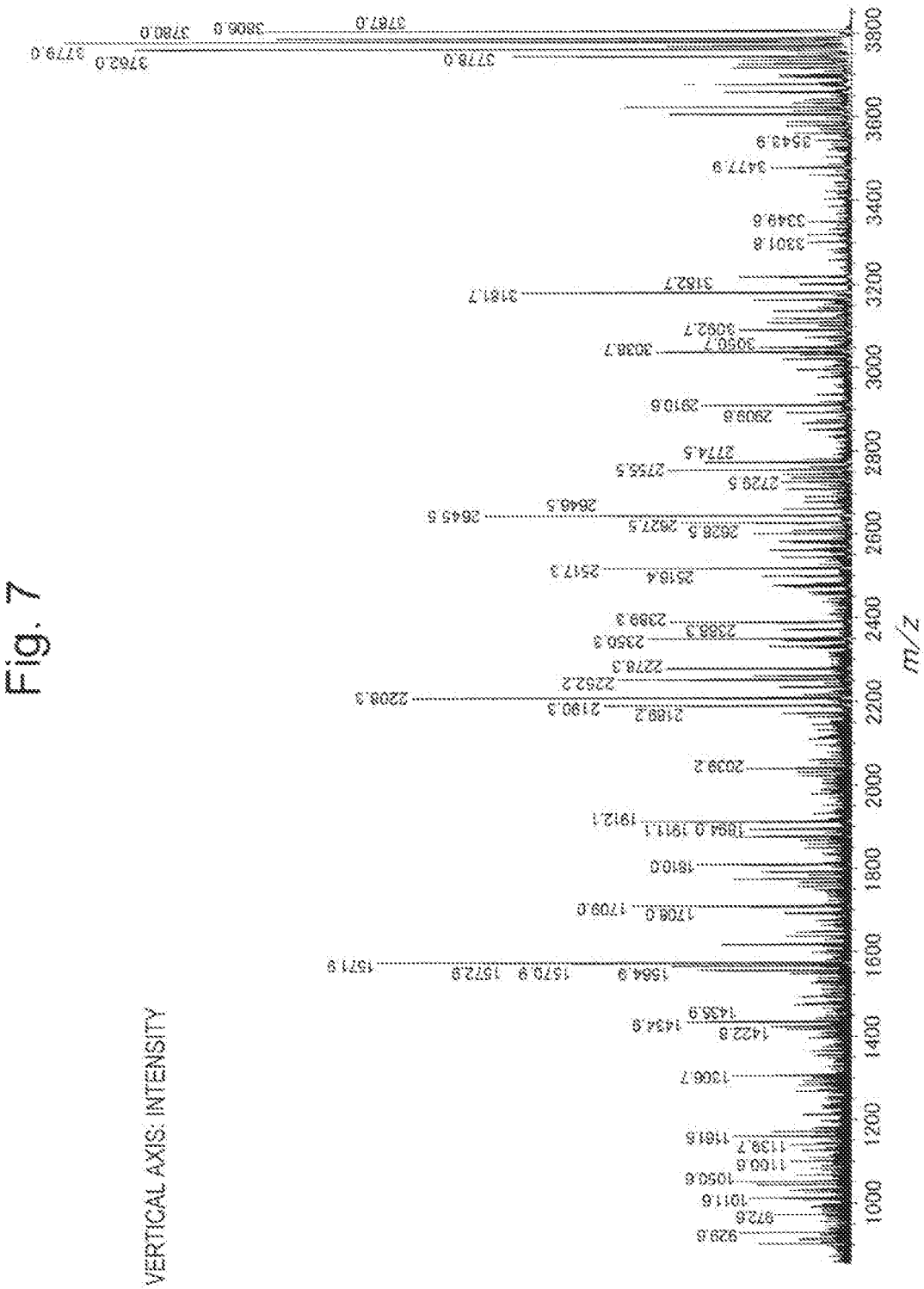
FIG. 7 shows a product ion spectrum obtained in tandem mass spectrometry of a molecule corresponding to a peak at m/z 3,823 observed in a mass spectrum when an *E. coli* K-12 strain has been cultured in a medium containing glucose.

FIG. 7 is a diagram showing a product ion spectrum obtained by tandem mass spectrometry. As a result of data analysis of this product ion spectrum, it was estimated that the molecule corresponding to m/z 3823 was a peptide having an amino acid sequence of "AETTTTPAPTATTT-KAAPAKTTHHKKQHKAAPAQKAQ" (SEQ ID NO: 2). This peptide was found to correspond to the 22th to 58th amino acids in the amino acid sequence of the acid shock protein of the *E. coli* K-12 strain (SEQ ID NO: 1). A similar analysis was performed, and the specific peak corresponding to m/z 2371 was estimated to correspond to the 59th to 79th amino acids in the amino acid sequence of the acid shock protein. The specific peak corresponding to m/z 2401 was estimated to correspond to the 80th to 102nd amino acids in the amino acid sequence of the acid shock protein.

Third Example

In Third Example, the *E. coli* K-12 strain was used as a sample, a difference between the first condition and the second condition was defined as the oxygen concentration of the gas in contact with the *E. coli* K-12 strain during culture, and a specific peak was detected.

Culture and Mass Spectrometry of *E. coli* K-12 Strain 20 mL of an aqueous solution containing 1% hipolypepton, 0.2% yeast extract, and 0.1% magnesium sulfate was prepared as a medium, and the *E. coli* K-12 strain was added to the medium. The medium to which the *E. coli* was added was dispensed in 10 mL portions, and one of the aliquots was set to a low oxygen concentration (0.5% or less) using an anaerobic culture system (AnaeroPack, Mitsubishi Gas Chemical Company, Inc.). Under conditions of 37° C. and 24 hours, the *E. coli* was cultured in the medium which had been set to a low oxygen concentration and the medium which had not been set to a low oxygen concentration, respectively. The culture solutions obtained after the culture were centrifuged, the supernatants were discarded, and 100 μL of an aqueous solution of 50% acetonitrile and 2.5% trifluoroacetic acid was added to the remaining bacterial cells to suspend them. The suspended solutions were centrifuged, and respective supernatants were collected individually. The collected supernatants were diluted 400 times or 1,600 times with 50% acetonitrile aqueous solution, and 0.5 μL of each diluted supernatant was dropped on a plate for MALDI mass spectrometry, and dried. 2.5 mg/mL CHCA was added to the dried samples so that CHCA was overlaid on the samples, and the resulting samples were dried again and subjected to time-of-flight mass spectrometry using the MALDI mass spectrometer (AXIMA Performance, manufactured by Shimadzu Corporation).

Figure 8:
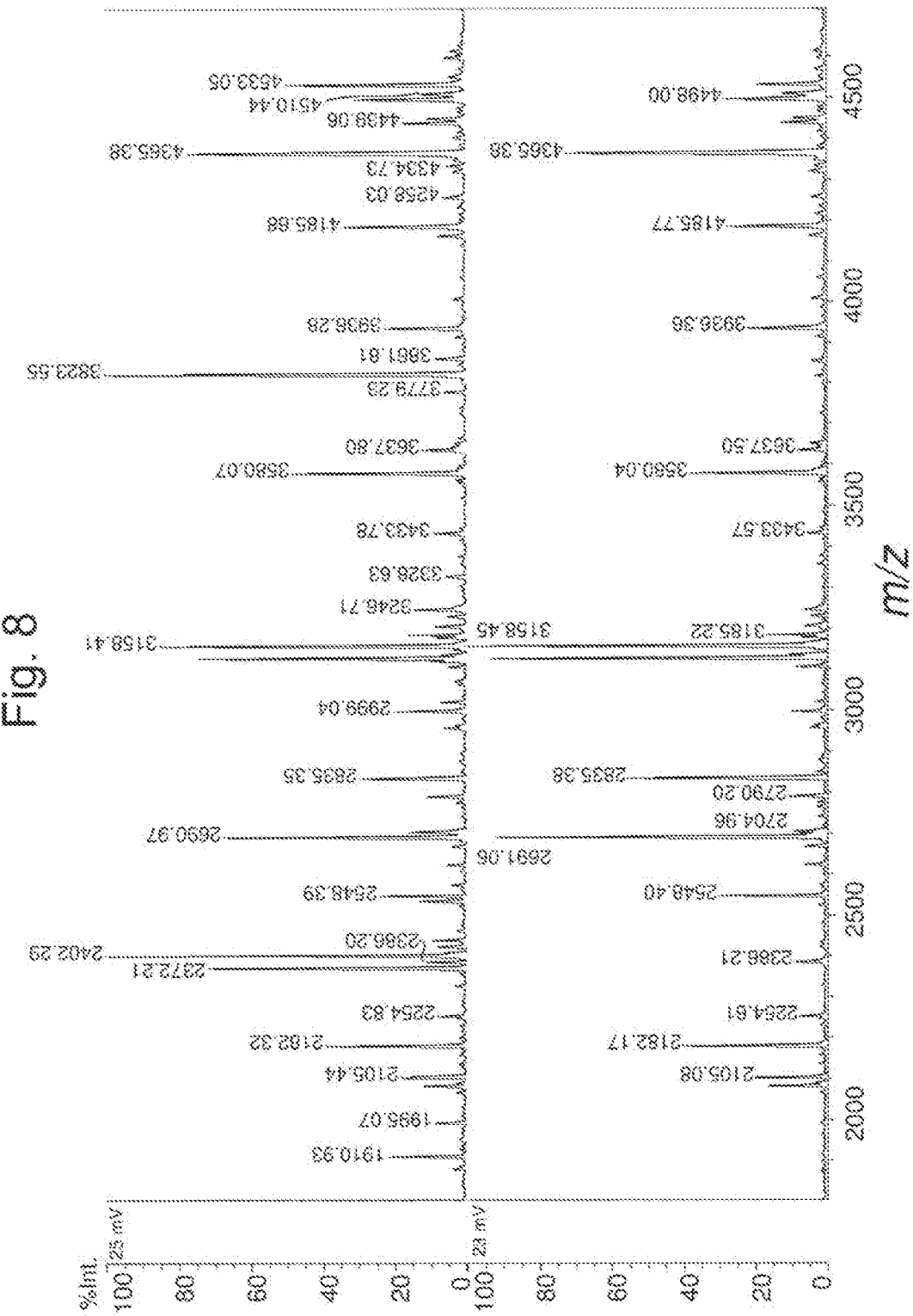
FIG. 8 shows mass spectra obtained by culturing *E. coli* K-12 strains under a low oxygen concentration (upper row) and a normal oxygen concentration (about 20%) (lower row), respectively, and performing mass spectrometry on substances produced by the bacteria.

FIG. 8 is a diagram showing a mass spectrum (upper row) obtained from microorganisms cultured under a low oxygen concentration and a mass spectrum (lower row) obtained from microorganisms cultured without being set to a low oxygen concentration. In a case where the E. coli K-12 strain was cultured under a low oxygen concentration, specific peaks at m/z 2371, m/z 2401, and m/z 3823 were observed in the obtained mass spectrum in comparison with the case of culturing without being set to a low oxygen concentration. The specific peaks were considered to correspond to the same molecule (acid shock protein) as the specific peak when cultured in a medium containing sugar. Therefore, it was found that this molecule could be expressed even when cultured under anaerobic conditions. In other words, it is possible to acquire the information on the classifications or characteristics of microorganisms by utilizing the characteristics that the acid shock protein is expressed or not expressed when cultured under anaerobic conditions. Further, it is also possible to acquire the information on the classifications or characteristics of microorganisms utilizing a difference in the value of m/z derived from this molecule.

Fourth Example

In Fourth Example, *Acinetobacter* was used as a sample, a difference between the first condition and the second condition was defined as the presence or absence of sugar in a medium, and a specific peak was detected.

Concerning Sample

As a sample, an environmental isolate of *Acinetobacter* was prepared. The environmental isolate of *Acinetobacter* was collected from human feces, and applied to a solid medium to obtain an isolate. Then, the isolate was identified as *Acinetobacter* by MALDI microorganism identification.

Culture and Mass Spectrometry of *Acinetobacter*

10 mL of an aqueous solution containing 1% hipolypepton, 0.2% yeast extract, and 0.1% magnesium sulfate (IFO 802 medium) was prepared, and Acinetobacter was added to the resulting medium. 10 mL of an aqueous solution containing 0.5% hipolypepton, 0.5% yeast extract, 0.5% glucose, and 0.1% magnesium sulfate (IFO 804 medium) was prepared, and *Acinetobacter* was added to the resulting medium. *Acinetobacter* was cultured in both the media under conditions of 37° C. and 18 hours. After the culture, respective culture solutions were centrifuged, the supernatants were discarded, and 100 µL of an aqueous solution of 2.5% trifluoroacetic acid and 50% acetonitrile was added to the remaining bacterial cells to suspend them. The suspended solutions were centrifuged, and the supernatants were collected. The collected supernatants were diluted 100 times with 50% acetonitrile aqueous solution, and 0.5 µL of each diluted supernatant was dropped on a plate for MALDI mass spectrometry, and dried. 0.5 µL of 2.5 mg/mL CHCA was added to the dried samples so that CHCA was overlaid on the samples, and the resulting samples were dried again and subjected to time-of-flight mass spectrometry using the MALDI mass spectrometer (AXIMA Performance, manufactured by Shimadzu Corporation).

Figure 9:
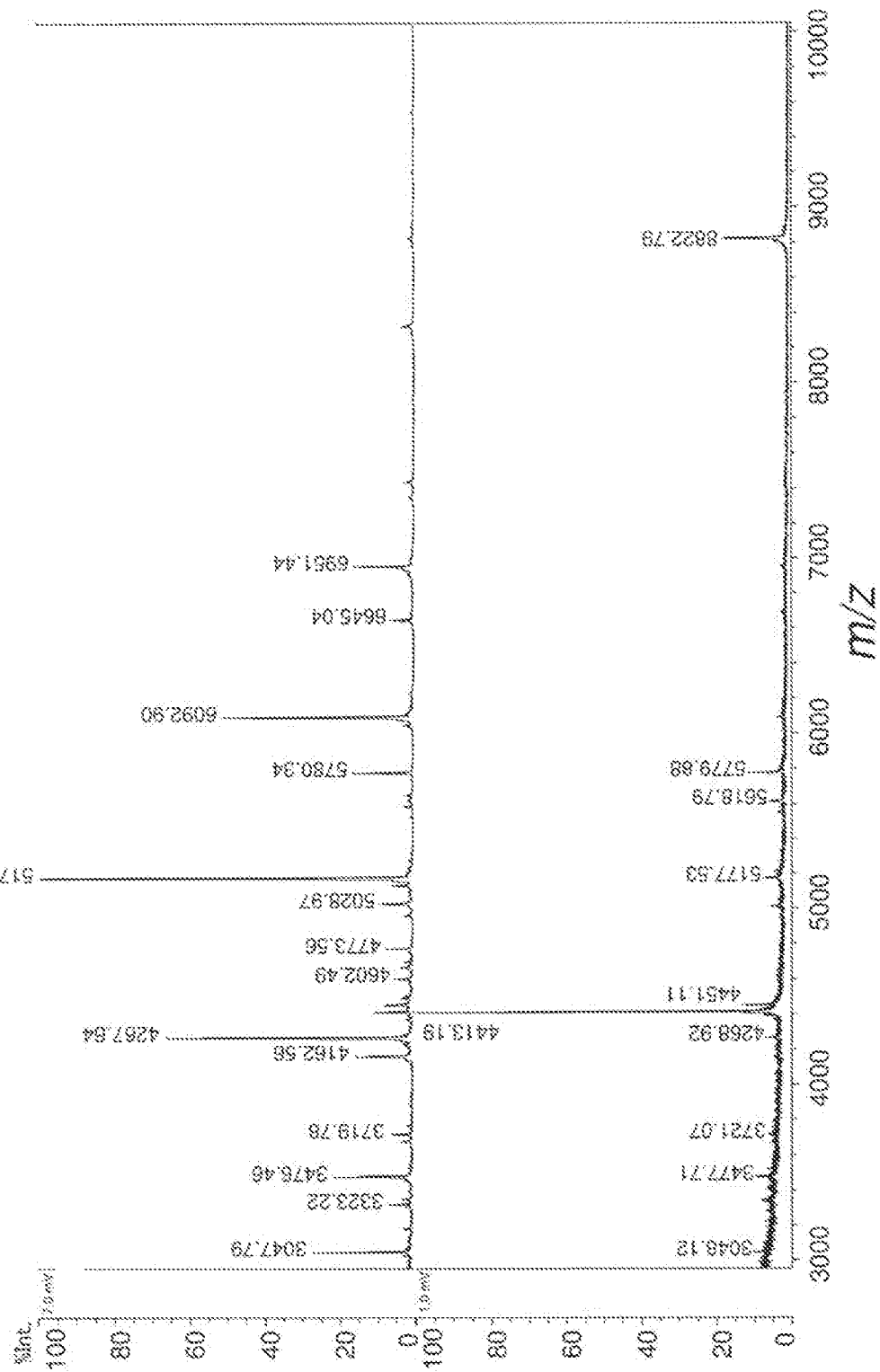
FIG. 9 shows mass spectra obtained by culturing *Acinetobacter* in a medium containing glucose (upper row) and a medium containing no glucose (lower row), respectively, and performing mass spectrometry on substances produced by the bacteria.

FIG. 9 is a diagram showing a mass spectrum obtained from *Acinetobacter* after cultured in a medium obtained by adding no glucose (upper row) and a mass spectrum obtained from *Acinetobacter* cultured in a medium obtained by adding glucose (lower row). In a case where the *Acinetobacter* was cultured in the medium obtained by adding glucose, a specific peak at 8822 was observed in the obtained mass spectrum in comparison with the case of culturing in the medium obtained by adding no glucose. Therefore, a phenomenon in which a molecule responding to this condition is expressed when cultured in the medium obtained by adding glucose is observed not only in E. coli but also in other microorganisms, indicating that the analysis method of the above-described embodiment is versatile. Although m/z 4413 can also be said to be a specific peak, this peak corresponds to a divalent ion corresponding to the specific peak at m/z 8822.

Fifth Example

In Fifth Example, an E. coli K-12 strain and an E. coli JM 109 strain were used as samples, a difference between the first condition and the second condition was defined as the presence or absence of sugar in a medium, and glucose and lactose were used as the sugars. The appearing specific peaks varied due to the change in sugar, and this was utilized to identify E. coli of two different strains.

Culture and Mass Spectrometry of E. coli K-12 Strain and E. coli JM 109 Strain (Presence or Absence of Glucose)

The E. coli K-12 strain was divided into two. One of the strains was cultured in a medium prepared by adding glucose (0.5 mass %) to an IFO 802 medium and the other strain was cultured in an IFO 802 medium, under conditions of 37° C. and 18 hours. The cultured microorganisms were centrifuged, the supernatants were discarded, and a trifluoroacetic acid-acetonitrile aqueous solution was added to the remaining bacterial cells to suspend them. The suspended solutions were centrifuged, and the supernatants were collected. The collected supernatants were diluted with an acetonitrile aqueous solution, dropped on a plate for MALDI mass spectrometry, and dried. CHCA as a matrix was added to the dried samples, and the resulting samples were dried again and subjected to time-of-flight mass spectrometry using the MALDI mass spectrometer (AMNIA Performance, manufactured by Shimadzu Corporation).

Similarly to the case of the E. coli K-12 strain, in the case of the E. coli JM 109 strain, the strains were cultured in a medium obtained by adding glucose (0.5 mass %) to an IFO medium and a medium obtained by adding no glucose to an IFO 802 medium, respectively, and samples were prepared in a similar manner to the method described above, and subjected to mass spectrometry.

FIG. 10 is a diagram showing a mass spectrum (the first row from the top) obtained from a K-12 strain cultured in a medium obtained by adding glucose, a mass spectrum (the second row from the top) obtained from a K-12 strain cultured in a medium obtained by adding no glucose, a mass spectrum (the third row from the top) obtained from a JM 109 strain cultured in a medium obtained by adding glucose, and a mass spectrum (the fourth row from the top) obtained from a JM 109 strain cultured in a medium obtained by adding no glucose. Similarly to the case of the E. coli K-12 strain, in the case of the E. coli JM 109 strain, specific peaks at m/z 2371, m/z 2401, and m/z 3823 were observed in the resulting mass spectra when cultured in the medium containing glucose (see rectangular portions P1 and P2 surrounded by broken lines). That is, the E. coli JM 109 strain also had a gene of the acid shock protein, and the gene was expressed when cultured in the medium containing glucose.

Culture (Addition of Lactose) and Mass Spectrometry of E. coli K-12 Strain and E. coli JM 109 Strain The E. coli K-12 strain and the E. coli JM 109 strain were each cultured in a medium prepared by adding lactose (1 mass %) to an IFO 802 medium under conditions of 37° C. and 18 hours. The cultured microorganisms were centrifuged, the supernatants were discarded, and a trifluoroacetic acid-acetonitrile aqueous solution was added to the remaining bacterial cells to suspend them. The suspended solutions were centrifuged, and the supernatants were collected. The collected supernatants were diluted with an acetonitrile aqueous solution, dropped on a plate for MALDI mass spectrometry, and dried. CHCA as a matrix was added to the dried samples, and the resulting samples were dried again and subjected to time-of-flight mass spectrometry using the MALDI mass spectrometer (AXIMA Performance, manufactured by Shimadzu Corporation).

FIG. 11 is a diagram showing a mass spectrum obtained from a JM 109 strain cultured in a medium obtained by adding lactose (upper row) and a mass spectrum obtained from a K-12 strain cultured in a medium obtained by adding lactose (lower row). In the case of the E. coli K-12 strain, a specific peak was observed similarly to the case where glucose was added in FIG. 10. Meanwhile, in the case of the E. coli JM 109 strain, no specific peak was observed similarly to the case where glucose was not added in FIG. 10 (see arrows A1, A2, and A3). In other words, the E. coli K-12 strain and the E. coli JM 109 strain similarly expressed the acid shock protein in the medium obtained by adding glucose, whereas in a case where lactose was added, the E. coli K-12 strain expressed the acid shock protein, but the E. coli JM 109 strain did not express the acid shock protein. As described above, it is possible to identify strains of bacteria using the fact that patterns of mass spectra obtained by changing the types of sugars are different.

The disclosure of the following priority application is incorporated herein by reference.

Japanese Patent Application No. 2019 071663 (filed on Apr. 3, 2019)

---

The invention claimed is:

1. An analysis method comprising:
   a sample preparing step of preparing a sample containing microorganisms;
   a first-data obtaining step of obtaining a first data by placing the microorganisms contained in the sample under a first condition and then performing a first mass spectrometry on a substance produced by the microorganisms;
   a second-data obtaining step of obtaining a second data by placing microorganisms of a same type as the microorganisms contained in the sample under a second condition and then performing a second mass spectrometry on a substance produced by the same type of microorganisms;
   a reference-data preparing step of preparing a reference data in which a classification or a characteristic of each of a plurality of types of microorganisms is associated with a data obtained in a mass spectrometry of a substance produced by the each of the plurality of types of microorganisms; and
   an information obtaining step of obtaining information on characteristics or classifications of the microorganisms contained in the sample on a basis of a difference between the first data and the second data as well as the reference data,
   wherein
   the first condition and the second condition differ in a sugar concentration or an oxygen concentration in a condition under which the microorganisms are placed.

2. The analysis method according to claim 1, wherein:
   in the sample preparing step, the sample containing microorganisms are divided into a first sample and a second sample;
   in the first-data obtaining step, microorganisms contained in the first sample are placed under the first condition and then the first mass spectrometry is performed on a substance produced by the microorganisms contained in the first sample; and
   in the second-data obtaining step, microorganisms contained in the second sample are placed under the second condition and then the second mass spectrometry is performed on a substance produced by the microorganisms contained in the second sample.

3. The analysis method according to claim 1, wherein the first condition and the second condition differ in the sugar concentration, and
   the sugar is at least one sugar selected from the group consisting of a monosaccharide, a disaccharide, a trisaccharide, and a tetrasaccharide.

4. The analysis method according to claim 3, wherein the sugar is at least one monosaccharide selected from the group consisting of allose, altrose, glucose, mannose, gulose, idose, galactose, talose, fucose, fuculose, rhamnose, psicose, fructose, sorbose, tagatose, ribose, arabinose, xylose, lyxose, ribulose, xylulose, deoxyribose, sedoheptulose, ketotetrose, erythrulose, aldotetrose, erythrose, threose, ketotriose, and aldotriose.

5. The analysis method according to claim 3, wherein the sugar is at least one disaccharide selected from the group consisting of sucrose, lactose, maltose, trehalose, turanose, and cellobiose.

6. The analysis method according to claim 3, wherein the sugar is at least one trisaccharide selected from the group consisting of raffinose, melezitose, and maltotriose.

7. The analysis method according to claim 3, wherein the sugar is at least one tetrasaccharide selected from the group consisting of acarbose and stachyose.

8. The analysis method according to claim 1, wherein the difference is presence or absence of a peak in a mass spectrum or a difference in intensity or area between peaks.

9. The analysis method according to claim 8, wherein the peak is a peak corresponding to an acid shock protein.

10. The analysis method according to claim 1, wherein an analysis sample for at least one of the first mass spectrometry or the second mass spectrometry is prepared using an aqueous solution containing at least one of an acid or an organic solvent.

11. The analysis method according to claim 10, wherein the acid is trifluoroacetic acid.

12. The analysis method according to claim 10, wherein the organic solvent is methanol, ethanol, isopropanol, or acetonitrile.

13. The analysis method according to claim 1, wherein; in the first mass spectrometry and the second mass spectrometry, ionization is performed by matrix-assisted laser desorption/ionisation or electrospray ionization.

14. The analysis method according to claim 1, wherein the information includes strains of microorganisms.

15. A microorganism identification method for analyzing microorganisms by the analysis method according to claim 1, wherein the information includes classifications of microorganisms, and
   the microorganisms are identified on a basis of the information.

16. A testing method for performing the analysis method according to claim 1, wherein the information includes characteristics of microorganisms, and
   the characteristics of the microorganisms are tested on a basis of the information.

* * * * *

SEQUENCE LISTING

<160> NUMBER OF SEQ ID NOS: 2

<210> SEQ ID NO 1
<211> LENGTH: 102
<212> TYPE: PRT
<213> ORGANISM: Escherichia coli K12

<400> SEQUENCE: 1

```
Met Lys Lys Val Leu Ala Leu Val Val Ala Ala Ala Met Gly Leu Ser
1               5                   10                  15

Ser Ala Ala Phe Ala Ala Glu Thr Thr Thr Thr Pro Ala Pro Thr Ala
                20                  25                  30

Thr Thr Thr Lys Ala Ala Pro Ala Lys Thr Thr His His Lys Lys Gln
            35                  40                  45

His Lys Ala Ala Pro Ala Gln Lys Ala Gln Ala Ala Lys Lys His His
        50                  55                  60

Lys Asn Thr Lys Ala Glu Gln Lys Ala Pro Glu Gln Lys Ala Gln Ala
65                  70                  75                  80

Ala Lys Lys His Ala Lys Lys His Ser His Gln Gln Pro Ala Lys Pro
                85                  90                  95

Ala Ala Gln Pro Ala Ala
            100
```

<210> SEQ ID NO 2
<211> LENGTH: 37
<212> TYPE: PRT
<213> ORGANISM: Escherichia coli K12

<400> SEQUENCE: 2

```
Ala Glu Thr Thr Thr Thr Pro Ala Pro Thr Ala Thr Thr Thr Lys Ala
1               5                   10                  15

Ala Pro Ala Lys Thr Thr His His Lys Lys Gln His Lys Ala Ala Pro
                20                  25                  30

Ala Gln Lys Ala Gln
            35
```